Figure 1:
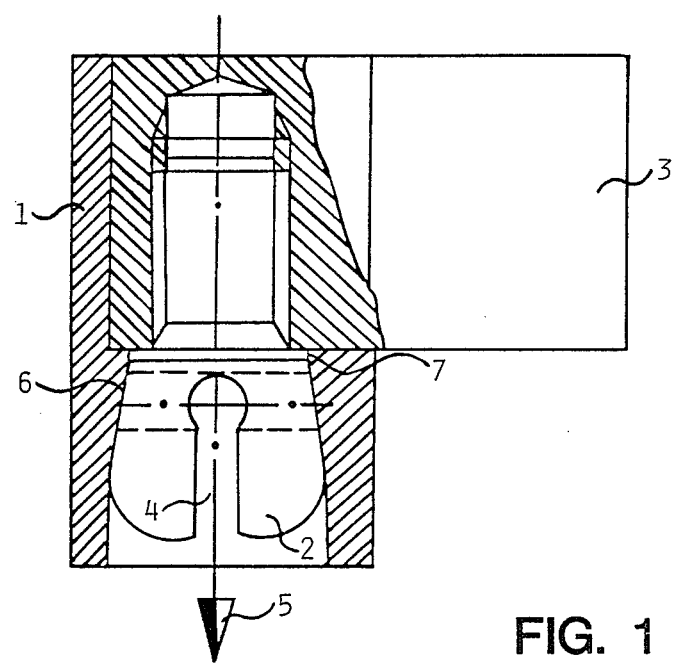

United States Patent [19]

Pilarek

[11] Patent Number: 4,756,691
[45] Date of Patent: Jul. 12, 1988

[54] SUPPORT FOR REMOVABLY FIXING A DENTAL PROSTHESIS ON A CROWN COVERING A PIVOT TOOTH, SO-CALLED ATTACHMENTS

[76] Inventor: Miroslaus Pilarek, Ostenstrasse 7, D-4840 Rheda-Wiedenbrück, Fed. Rep. of Germany

[21] Appl. No.: 459,540
[22] PCT Filed: May 4, 1982
[86] PCT No.: PCT/EP82/00093
 § 371 Date: Jan. 4, 1983
 § 102(e) Date: Jan. 4, 1983
[87] PCT Pub. No.: WO82/03763
 PCT Pub. Date: Nov. 11, 1982

[30] Foreign Application Priority Data

May 5, 1981 [AT] Austria .................................. 1975/81

[51] Int. Cl.⁴ ............................................. A61C 13/22
[52] U.S. Cl. ..................................................... 433/177
[58] Field of Search .................. 433/177, 173; 24/214, 24/213 R, 213 B, 213 CS

[56] References Cited

U.S. PATENT DOCUMENTS

| 702,857 | 6/1902 | Griswold | 433/177 |
| 866,304 | 9/1907 | Roach | 433/177 |
| 3,890,738 | 6/1975 | Bassani | 46/29 |

Primary Examiner—Robert Peshock
Attorney, Agent, or Firm—Max Fogiel

[57] ABSTRACT

The supports for removably fixing a dental prosthesis on a crown covering a pivot teeth are comprised of a single hollow base fixed to the crown and a laterally cross-split stud engaged in the base. To avoid an exclusively annular engagement and consequently prevent rapid wear of the parts, the base (1) and the stud (2) have a bearing surface (6) tapered in the engagement direction (5), preferably in the form of a truncated cone. Thus, there is provided a substantially more reliable fixing without unfavorably influencing the fabrication costs.

3 Claims, 1 Drawing Sheet

U.S. Patent    Jul. 12, 1988    4,756,691

SUPPORT FOR REMOVABLY FIXING A DENTAL PROSTHESIS ON A CROWN COVERING A PIVOT TOOTH, SO-CALLED ATTACHMENTS

The invention relates to a support for removably fixing a dental prosthesis on a crown covering a pivot tooth, so-called attachments, comprised of a sleeve-type socket fixed to the crown and a stud, cross-split on the end face, which starts from the dental prosthesis and can engage as a plug in the socket.

In addition to profile attachments of very diverse designs, anchorages of the abovementioned type are known in dentistry practice. The disadvantage is that the studs being used at present bear against the socket and are held only annularly. However, on regular removal and reinsertion of the dental prosthesis, such annular contact produces extensive wear phenomena which necessarily impair the strength of the fixing. If this strength is to be restored, the only possibility, and hence the customary method, is to widen the stud by bending the slots open, but this leads to destruction of the stud, particularly if it is done repeatedly.

It is now the object of the invention to make a support available which, while avoiding the disadvantages hitherto occurring, guarantees a long life of the removable fixing. At the same time the elastic properties of the stud representing the socket are to be improved.

The object according to the invention is achieved when the socket forms, with the stud engaging therein, a common bearing surface (6) uniformly tapered in the engagement direction of the stud. The common bearing surface of the socket and the stud can here preferably have the form of a truncated cone or a convex form.

The abovementioned features eliminate the earlier annular contact between the stud and the socket and the resulting wear of the former. For a further improvement of the accuracy of the fit of the durable removable fixing thus achieved, it is additionally proposed that the socket has a cylindrical shoulder before the tapered bearing surface, as viewed in the engagement direction of the stud. Moreover, yielding of the stud, which is extremely important for the removal and insertion of the dental prosthesis, can be substantially improved when the slots of the stud have a recess of keyhole-shaped cross-section on their inward end.

Figure 2:
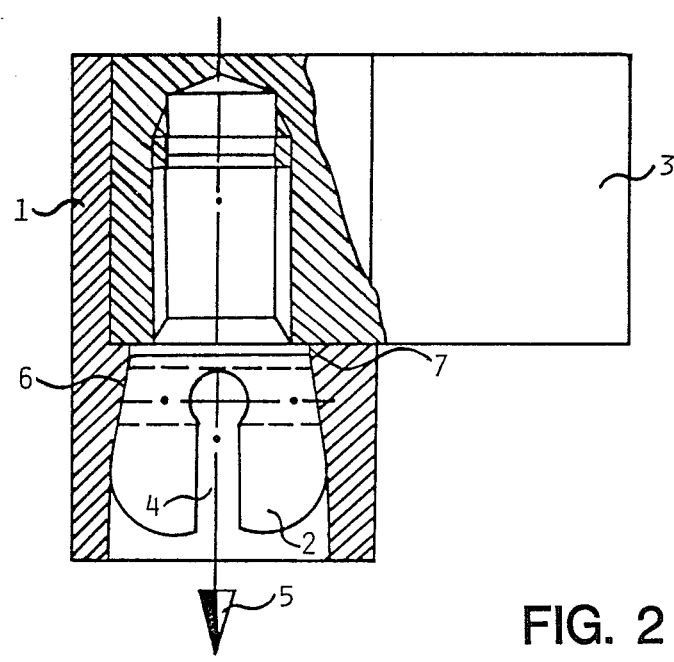

Two illustrative embodiments of the subject of the application are explained below by reference to the drawing. FIGS. 1 and 2 here show sectional representations of slightly different anchorages for dental prostheses.

As can be seen from the drawings, the supports shown therein are each composed of a sleeve-type socket 1, to be fixed to the crown of a pivot tooth, and a stud 2 which is received by this socket 1 and is screwed into a fixing arm 3 leading to the dental prosthesis. To enable the stud 2 serving as the plug to engage in the socket 1, it is designed to be yielding as the result of slots 4 which extend crosswise on the end face and which have recesses of keyhole-shaped cross-section on the inward end.

In both illustrative embodiments, the socket 1 forms, with the stud 2 engaging therein, a common bearing surface 6 uniformly tapered in the engagement direction 5 of the stud, the bearing surface having the form of a truncated cone in the case of FIG. 1, and a convex form in the case of FIG. 2. To ensure perfect centering of the stud 2, the socket 1 is also provided with a cylindrical shoulder 7 before the tapered bearing surface 6, as viewed in the engagement direction 5 of the stud 2. This shoulder 7 also serves to minimise wear of the socket 1 at its engagement opening.

I claim:

1. A support for removably connecting a dental prosthesis with a crown mounted on a foundation tooth, comprising: a sleeve-shaped socket attached to the crown; a plug-shaped member extending from the prosthesis and insertable into said socket, said plug-shaped member having slots extending crosswise on the end face of said plug-shaped member; said socket and plug-shaped member forming together a common bearing surface having a shape of a truncated cone tapering uniformly with larger cross-sectional area of said tapered truncated cone facing removal direction of said plug-shaped member.

2. A support as defined in claim 1, wherein said socket has a cylindrical shoulder before said common bearing surface when viewed in engagement direction of said plug-shaped member.

3. A support as defined in claim 1, wherein said slots on the end face of said plug-shaped member have a recess of keyhole-shaped cross-section on their inward end.

* * * * *